March 20, 1956 E. S. BOERNER Plant Pat. 1,462
CHRYSANTHEMUM PLANT
Filed April 15, 1955
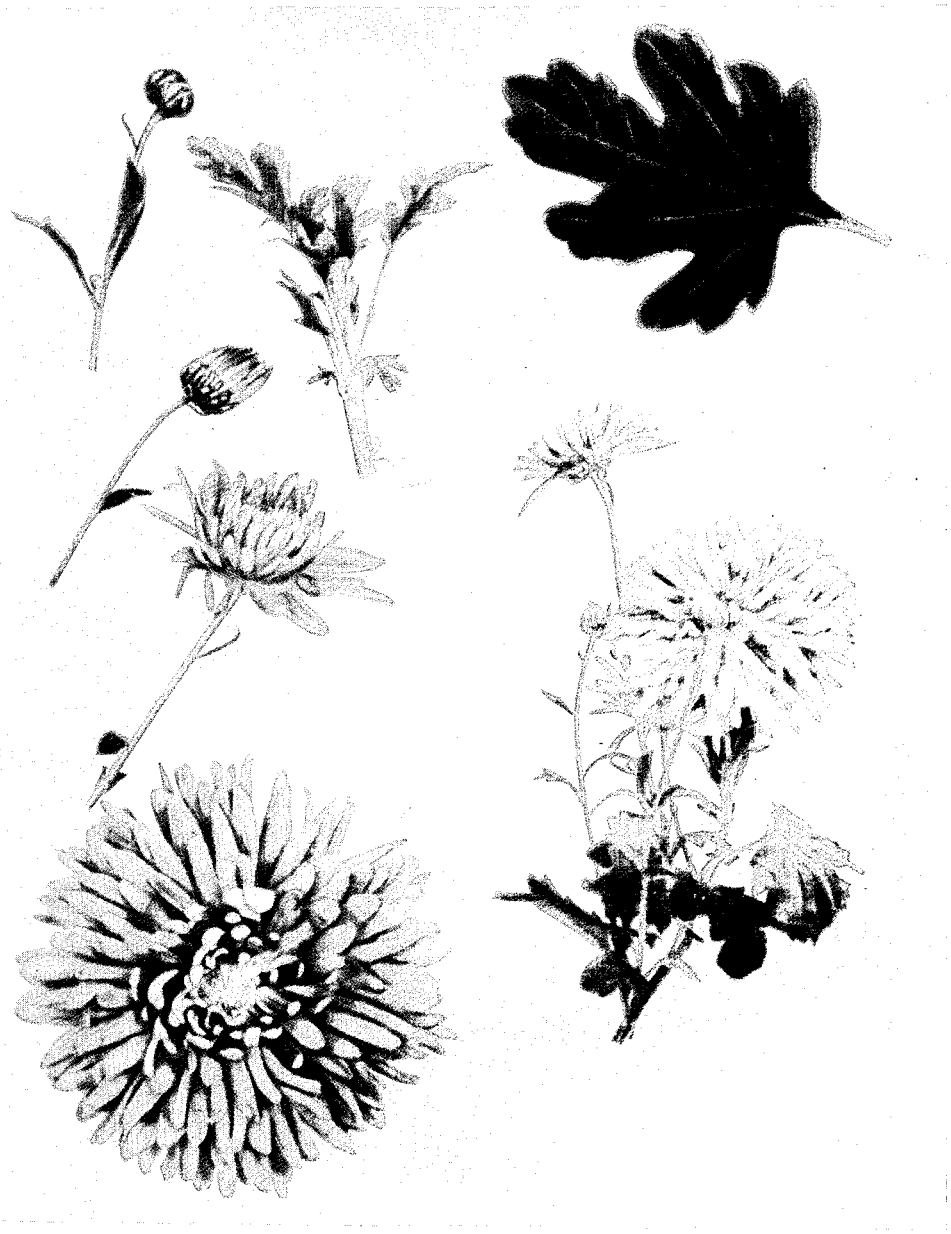
Inventor.
E. S. Boerner
By: Robb & Robb
Attorneys.

United States Patent Office

Plant Pat. 1,462
Patented Mar. 20, 1956

1,462

CHRYSANTHEMUM PLANT

Eugene S. Boerner, Newark, N. Y., assignor to Jackson & Perkins Company, Newark, N. Y., a corporation of New York Application April 15, 1955, Serial No. 501,756

1 Claim. (Cl. 47—60)

The present invention relates to a new and distinct variety of chrysanthemum plant of the hardy outdoor decorative type, which was originated by me by crossing the variety "Maroon'N Gold" (unpatented) with the vaiety "Indiana" (unpatented).

The primary objective in making this cross was to produce a new chrysanthemum variety of the hardy outdoor type, but which is early-blooming and bears large red flowers, thus combining the early-blooming habit of the variety "Maroon'N Gold" with large red flowers which are characteristic of the parent variety "Indiana." This objective was fully achieved, as evidenced by the fact that my new variety is particularly characterized by its early period of bloom and by the unfading distinctive red color of its flowers. A still further important identifying characteristic of my new variety is the irregular rounded serrulations of its foliage. Together, these characteristics definitely differentiate my new variety from its parents, as well as from all other varieties of its class of which I am aware.

Asexual reproduction of my new variety by top cuttings and by underground runners, as performed by me at Newark, New York, shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: "Maroon'N Gold × "Indiana."
Classification: Decorative.
Growth: From 21 inches to 24 inches.
Cold resistance: Winter hardy; frost resistant flowers.

Blooming period: In the Newark, New York, climatic area, blooming starts about September 5 and the plant is very free-blooming until severe freezing temperatures in October or November of the average season.

FLOWER (Observations made from specimens grown in a field at Newark, New York, about mid-morning in the early part of October.)

Bud:

*Color.*—When sepals first divide—Pomegranate Purple, Plate 12. When petals begin to unfurl—Morocco Red, Plate 1, lightly overcast with Nopal Red, Plate 1. When half blown: Inside of petals—Brazil Red, Plate 1; outside of petals—Nopal Red, Plate 1, lightly overcast with Grenadine Red, Plate 2.

*Peduncle.* — Strong; upright. Color — Absinthe Green, Plate 31.

Bloom:

*Size.*—From 3½ inches to 4 inches.
*Stem.*—Stiff; good cutting.
*Form.*—Decorative.
*Petalage.*—Double.
*Color.* — Center of flower — Brazil Red, Plate 1, slightly overcast with Scarlet, Plate 1. Outer petals—Nopal Red, Plate 1, lightly overcast with Scarlet, Plate 1. Base of petals —Lemon Yellow, Plate 4. Reverse of petals—Apricot Yellow, Plate 4, lightly overcast with Scarlet Red, Plate 1. Inside of petals—Brazil Red, Plate 1, lightly overcast with Nopal Red, Plate 1.
*Petals.*—Texture—medium stiff. Form—long.
*Fragrance.*—Characteristic chrysanthemum.

PLANT

Form: Upright.
Growth: Rounded; full.
Foliage:

*Size.*—Medium.
*Quantity.*—From normal to heavy.
*Shape.*—Has deep irregular serrulations.
*Color.*—Upper side—Forest Green, Plate 17. Reverse side—Light Cress Green, Plate 31.
*Texture.*—Leathery.

I claim:

A new and distinct variety of chrysanthemum plant of the decorative type, substantially as herein shown and described, characterized particularly as to novelty by the irregular rounded serrulations of its foliage, its early-blooming habit, and its large unfading red flowers.

No references cited.